United States Patent [19]

Allard et al.

[11] Patent Number: 5,425,781
[45] Date of Patent: Jun. 20, 1995

[54] ANKLE CONNECTOR FOR PROSTHETIC FOOT

[75] Inventors: Paul Allard, Pierrefonds; Jean Dansereau, Sainte-Thérèse; François Trudeau, Montréal; Mathieu Lussier, Fabreville, all of Canada

[73] Assignee: Université de Montréal, Montréal, Canada

[21] Appl. No.: 181,028

[22] Filed: Jan. 14, 1994

[51] Int. Cl.⁶ .............................. A61F 2/62; A61F 2/66
[52] U.S. Cl. ........................................ 623/38; 623/52; 623/55; 623/47
[58] Field of Search .................. 623/38, 47, 53, 50, 623/52, 55

[56] References Cited

U.S. PATENT DOCUMENTS

| | | | |
|---|---|---|---|
| 3,400,408 | 9/1968 | Garcia | 623/38 X |
| 4,395,783 | 8/1983 | Eyre et al. | |
| 4,413,360 | 11/1983 | Lamb et al. | |
| 4,446,580 | 5/1984 | Furuya et al. | 623/53 |
| 4,645,509 | 2/1987 | Poggi et al. | |
| 5,116,385 | 5/1992 | Allard et al. | 623/55 |
| 5,156,632 | 10/1992 | Wellershaus | |
| 5,158,570 | 10/1992 | Schey et al. | 623/52 |
| 5,226,918 | 7/1993 | Silagy et al. | 623/32 |

FOREIGN PATENT DOCUMENTS

| | | | |
|---|---|---|---|
| 2054588 | 5/1992 | Canada | |
| 9115171 | 10/1991 | WIPO | 623/53 |
| 93024080 | 12/1993 | WIPO | 623/53 |
| 94010942 | 5/1994 | WIPO | 623/53 |

Primary Examiner—David H. Willse
Attorney, Agent, or Firm—Pierre Lespérance; François Martineau

[57] ABSTRACT

An exoskeletal (or endoskeletal) ankle connector for use in fixedly securing a prosthetic foot to a prosthetic leg. The foot has an elongated cantilever spring type keel. The keel defines an elongated forefoot part, an ankle part and a heel part merging the ankle part with the forefoot part. The keel ankle part is provided with a cavity. The leg has a bottom end with an integral bolt with the bolt having a free projecting threaded stem. The ankle connector consists of a casing sized to conformingly engage into and snugly fit within the keel cavity; the casing is releasably anchored by bolts to the keel inside the keel cavity; an annular gear screw assembly within the casing is engaged threadingly by the leg bolt stem to progressively draw toward one another the casing and the leg bottom end along the bolt stem upon inducing rotation of the foot relative to the leg; and an endless screw meshes tangentially with the gear of the screw assembly to anchor the foot at a selected angular orientation relative to the leg upon the foot remaining rotationless relative to the leg. Operative access to the endless screw is enabled without there being required the piercing of an access bore neither through the heel part nor through the forefoot part.

4 Claims, 3 Drawing Sheets

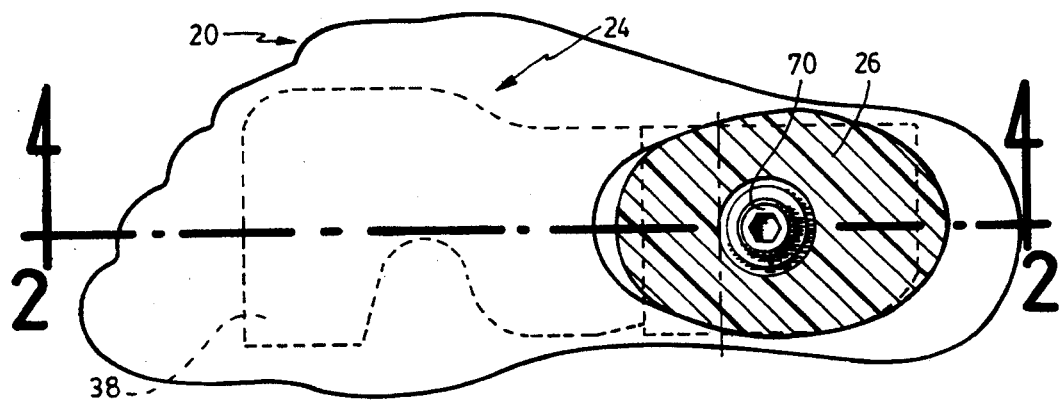
Fig.1
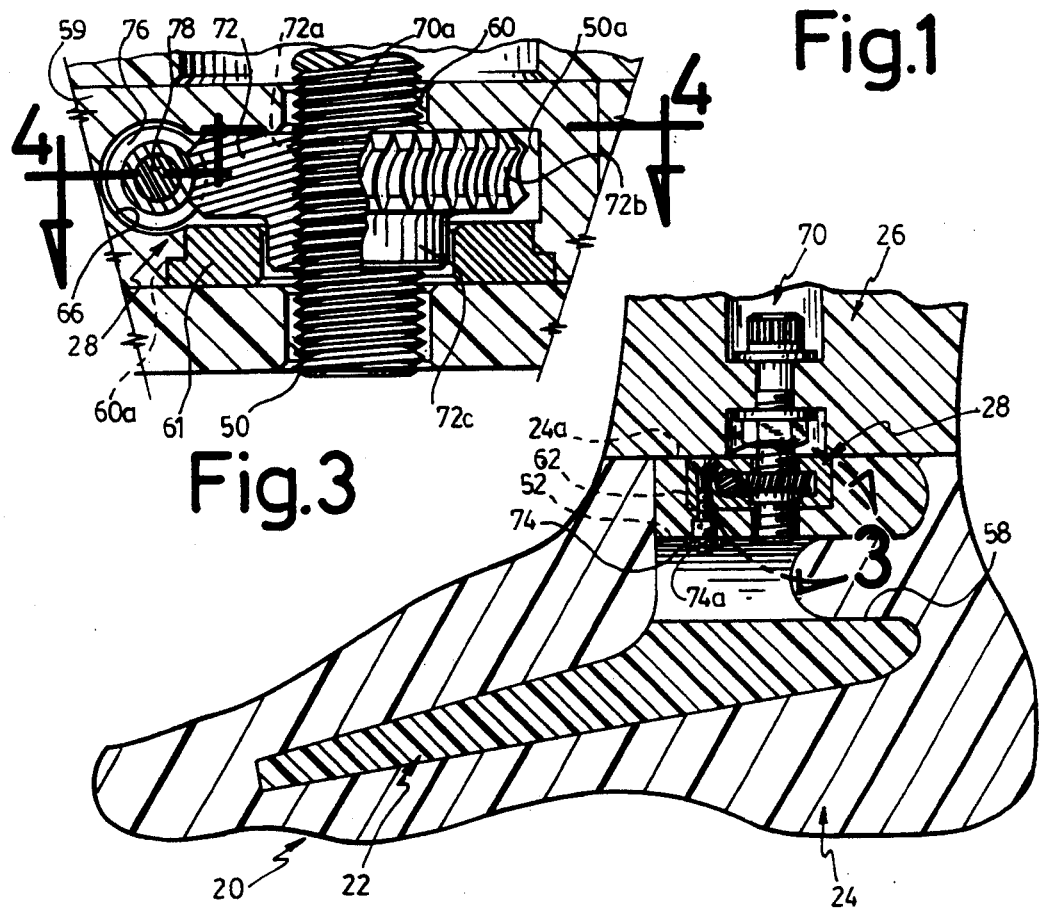
Fig.3
Fig.2

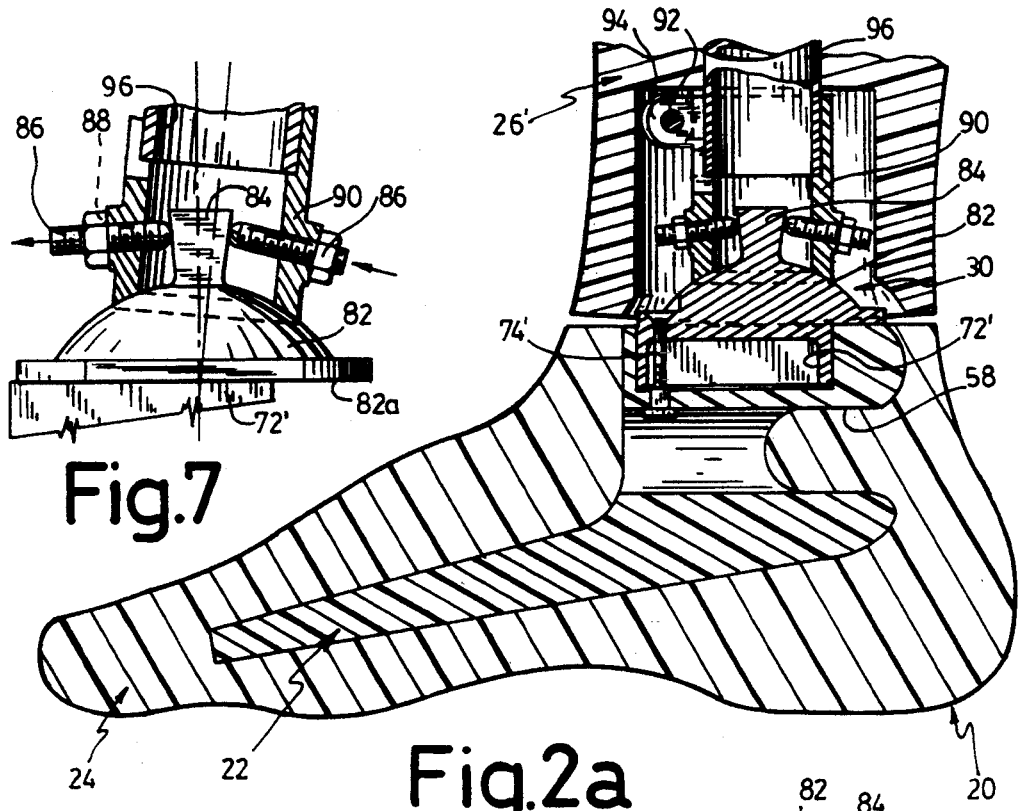
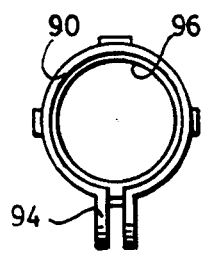
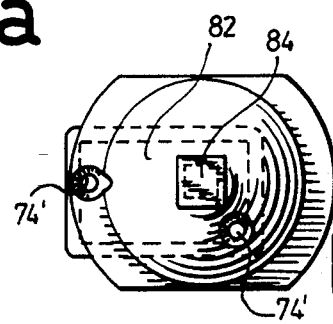
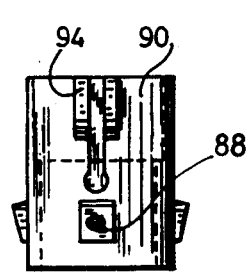
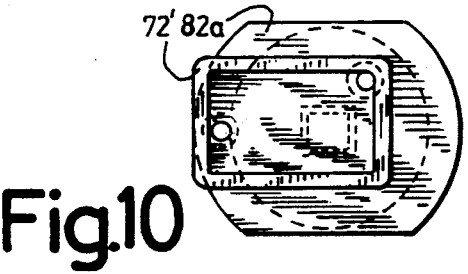

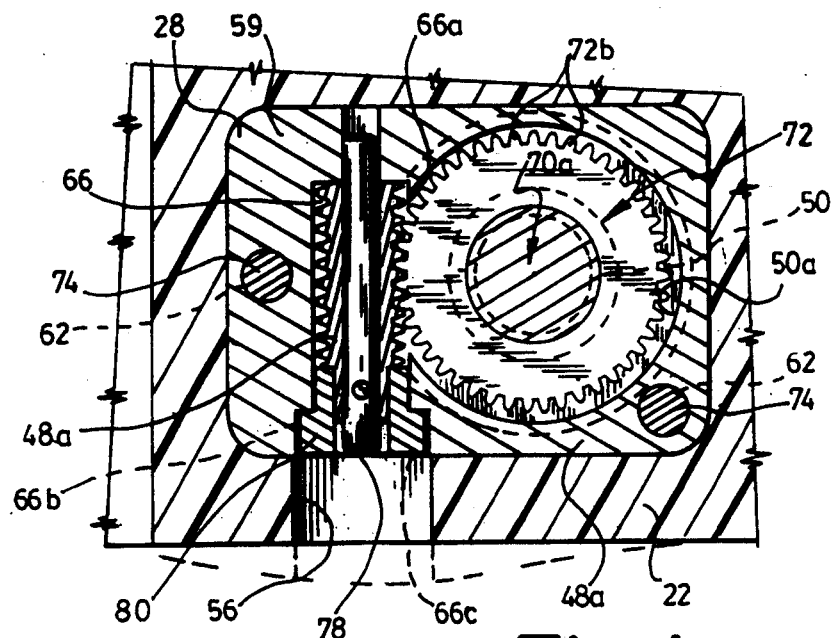
Fig.4
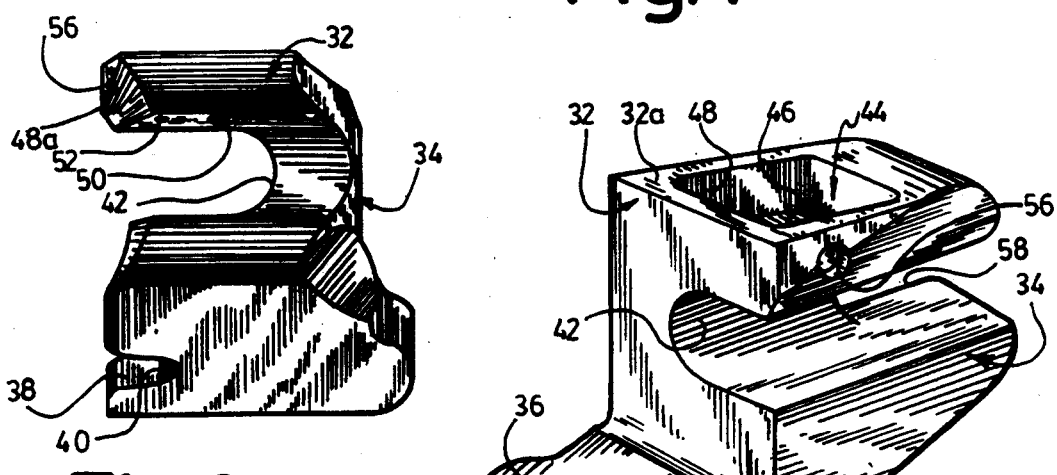
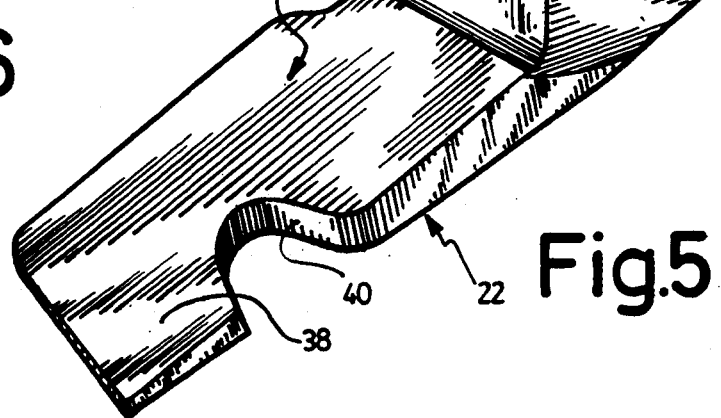
Fig.6
Fig.5

ANKLE CONNECTOR FOR PROSTHETIC FOOT

FIELD OF THE INVENTION

This invention relates to artificial leg part devices that are to fit the stump of amputated persons, for enabling same to at least partially resume life-like leg movement.

CROSS-REFERENCE DATA

U.S. Pat. No. 5,116,385 issued in 1992 in the name of the present single applicant, Université de Montréal—the joint inventors therein being: Paul ALLARD, Jean DANSEREAU, and Claude LÉVESQUE—, is hereby incorporated by way of reference to the present patent application—in which the joint inventors includes said Paul ALLARD and said Jean DANSEREAU, and also, the additional following two inventors: François TRUDEAU, and Mathieu LUSSIER.

BACKGROUND OF THE INVENTION

U.S. Pat. No. 5,116,385, issued on May 26, 1992 in the name of the present single applicant and designating two (dr Paul ALLARD and dr Jean DANSEREAU) of the four present joint inventors, discloses a prosthetic foot keel provided with means for enhancing medio-lateral stability during gait of the amputee. These means were embodied in an inward, medio-lateral forefoot portion extension of the prosthetic keel which, by extending the lever arm of the deformable keel, produced a medio-lateral propulsion capability at foot push off.

U.S. Pat. No. 4,395,783 issued 2 Aug. 1983 to the british company Vessa limited, discloses a conventional artificial leg with an endoskeletal type ankle attachment member. The shin member 12 (FIG. 1) is fitted with a prosthetic foot consisting of a relatively rigid, elastomeric-covered keel 41. The ankle base 42 is secured at its upper face to an ankle attachment member 38 and at its lower face to the keel 41 about a transverse (generally horizontal) ankle pivot 43. Bolt 24 engages (generally vertically, i.e. axially of the limb ) in the insert 39, to secure the ankle base 42 to the ankle attachment member 38.

U.S. Pat. No. 5,156,632 issued 20 Oct. 1992 to the german corporation *Otto Bock Orthopædische Industrie Besitzund Verwaltungs-Kommanditgesellschaft, Industriestraße* discloses another prosthetic foot, with artificial leg with another endoskeletal type, ankle attachment member, but with the prosthetic foot now being jointless. The stub-like foot adapter, 3, (with a semi-spherical upper surface) is for detachable connection to the overlying prosthetic limb.

U.S. Pat. No. 4,413,360 issued Nov. 8, 1983 to Steve LAMB and Larry LAMOREUX, discloses an ankle assembly for a prosthetic foot, being provided with means for heel height adjustment and heel securing in an optimum position for comfort of the amputee. A mechanism is interposed between an ankle block and a connected foot block with a pivot and associated adjustment screw for altering the fore and aft tilt of the foot block with respect to the ankle block. More specifically, screws 58, actuated by an Allen key, operate on a tilting casing 46, so as to be able to precisely adjust the orientation of the keel relative to the antero-posterior plane of the limb.

OBJECT OF THE INVENTION

An object of the invention is therefore to improve upon the prosthetic foot disclosed and claimed in U.S. Pat. No 5,116,385 (which issued to the present single applicant).

An important object of the invention is to provide endo- or exo-skeletal type ankle connectors for prosthetic limbs, which do not require piercing of a bore through the keel lower heel part for enabling access by the (prior art) adjusting screw tool.

A further important object of the invention is that the heel part of the keel of the above foot includes cavity means for dampening gait-borne cyclical ground forces at heel-strike, providing a medio-lateral mechanical feedback to the amputee at heel-strike.

SUMMARY OF THE INVENTION

Accordingly with the objects of the invention, there is disclosed an exoskeletal ankle connector for use in fixedly securing a prosthetic foot to a prosthetic leg, said foot of the type having an elongated cantilever spring type keel, said keel to be of the type defining an elongated forefoot part, an ankle part and a heel part merging said ankle part with said forefoot part, said keel ankle part to be provided with a cavity, said leg to be of the type having a bottom end with an integral bolt with said bolt having a free projecting threaded stem; said ankle connector consisting of: (a) a casing member, sized to conformingly engage into and snugly fit within said keel cavity; (b) anchoring means, for releasably anchoring said casing member to said keel inside said keel cavity; (c) screw means, to progressively draw toward one another said casing member and said leg bottom end along said bolt stem upon inducing rotation of said foot relative to said leg; and (d) tightening means, cooperating with said screw means to anchor said foot at a selected angular orientation relative to said leg upon said foot remaining rotationless relative to said leg; wherein there is free operative access to said tightening means.

Said selected angular orientation of the prosthetic foot could be, for example, within the sagittal plane of the leg. Advantageously, said casing member includes a first unthreaded channel with an enlarged intermediate annular chamber, said first channel for free through engagement by said leg bolt stem; said screw means defining an annular gear freely mounted within and retained by said annular chamber and defining radially inward teeth, said gear inward teeth for threadingly engaging said leg bolt threaded stem.

Profitably, said casing member further includes a second channel extending orthogonally of said first channel, said second channel opening into said annular chamber about an intermediate section of said second channel; said keel to include a boring in coaxial register with said second channel for enabling external access thereto, said keel boring to extend transversely of said sagittal plane of the leg; said annular gear further defining a radially outward concave surface provided with teeth; said tightening means defining an endless screw, extending inside said second channel for frictional rotational engagement within the casing member, said endless screw defining teeth threadingly engaging with said gear radially outward teeth tangentially of said annular gear; wherein cooperation of said endless screw with said annular gear provides tightening of said foot to said leg without any rotation of said foot relative to said leg for achieving a fine degree of adjustment in the orientation of said foot within said sagittal plane of the leg.

Preferably, said endless screw teeth define a very short pitch, to substantially prevent any time or wear induced loosening of said annular gear about said leg bolt stem.

In an alternate embodiment of the invention, there is disclosed an endoskeletal ankle connector for use in fixedly securing a prosthetic foot to a prosthetic leg, said foot of the type having an elongated cantilever spring type keel, said keel to be of the type defining an elongated forefoot part, an ankle part and a heel part merging said ankle part with said forefoot part, said keel ankle part to be provided with a cavity, said leg to be of the type being hollow and open at a bottom end mouth; said ankle connector consisting of: (a) a casing member, sized to conformingly engage into and snugly fit within said keel cavity; (b) anchoring means, for releasably anchoring said casing member to said keel inside said keel cavity; (c) a semi-spherical stub member, integral to said casing member, said stub member to engage into and be retained in the hollow of said leg; (d) means for fixedly securing said stub member to said leg inside the hollow of said leg; and (d) tightening means, cooperating with said fixedly securing means to anchor said foot at a selected angular orientation relative to said leg upon said foot remaining rotationless relative to said leg; wherein there is free operative access to said tightening means.

This invention also relates to the combination of a prosthetic foot with an exoskeletal ankle connector for fixedly securing said foot to a prosthetic leg, said foot consisting of cantilever spring monolithic member made from a substantially rigid, yet resiliently elastic material, and forming an elongated band defining one and another lateral side edges; said band formed of two coextensive integral parts including an elongated forefoot part and a C-shape aft heel part; the C-shape of said heel part being medio-laterally oriented and defining a straight, free, outer end portion, an opposite, straight, inner end portion substantially parallel to said outer end portion, and an arcuate portion integrally joining a fore fraction of said heel part inner and outer end portions, whereby the thus formed aft fraction of said heel part inner and outer end portions not joined by said arcuate portion define a sagittal gap spacing therebetween such that said aft fraction of the heel part outer end portion spacedly overlies the aft fraction of said heel part inner end portion, said gap spacing being of variable magnitude upon a load being applied against the aft end of said elastic heel part outer end to resiliently bias same toward the aft end of said heel part inner end; said heel part outer end portion further having attachment means for connection to an upper prosthesis; a flange projecting transversely from said another lateral side edge of said forefoot part integrally thereto; said band also including a curved part, integrally interconnecting said forefoot part and said heel part inner end portion, said curved part curved toward a plane intersecting said heel part free end portion, whereby said heel part, forefoot part and curved part extend substantially within a single sagittal plane, and said forefoot flange projecting outwardly from and about an axis orthogonal to said sagittal plane; wherein upon said cantilever spring member being fitted to an amputee's limb through said attachment means, said cantilever spring member, during gait, will absorb energy at said heel part during prosthetic foot heel strike, will store said energy, will transfer this stored energy to said curved part and forefoot part, and will restore said energy at foot push-off in such a way as to provide substantial medio-lateral control of the prosthetic foot during both loading and unloading of the prosthetic foot keel, as well as shock dampening capability at heel strike; wherein said attachment means is an exoskeletal ankle connector, said heel part outer end portion being provided with a cavity, said leg to be of the type having a bottom end with an integral bolt with said bolt having a free projecting threaded stem; said ankle connector consisting of: (a) a casing member, sized to conformingly engage into and snugly fit within said cantilever member cavity; (b) anchoring means, for releasably anchoring said casing member to said keel inside said cantilever member cavity; (c) screw means, to progressively draw toward one another said casing member and said leg bottom end along said bolt stem upon inducing rotation of said foot relative to said leg; and (d) tightening means, cooperating with said screw means to anchor said foot at a selected angular orientation relative to said leg upon said foot remaining rotationless relative to said leg; wherein there is free operative access to said tightening means.

BRIEF DESCRIPTION OF THE DRAWINGS

FIG. 1 is a top plan view of a right-hand side prosthetic foot, made through the artificial leg connected to the foot;

FIG. 2 is a sectional view along line 2—2 of FIG. 1, showing a first embodiment of limb connector adapted to fit an exoskeletal limb;

FIG. 2a is a view similar to FIG. 2, but showing an alternate embodiment of limb connector adapted to fit an endoskeletal, limb;

FIG. 3 is an enlarged view of the area circumscribed by ellipse 3 in FIG. 2, with the threaded screw gear being shown partly fragmented for clarity of the view;

FIG. 4 is a cross-section taken about line 4—4 of FIG. 3;

FIG. 5 is an isometric view of the keel proper of the prosthetic foot;

FIG. 6 is an aft end view of the keel of FIG. 5;

FIG. 7 is a detail of the endoskeletal connector member being isolated from most of the elements appearing in FIG. 2a, suggesting the axial play thereof;

FIGS. 8, 9 and 10 are a top plan view, an edge view, and a bottom plan view, respectively, of the endoskeletal connector member of FIG. 7; and FIGS. 11–12 are an end view and a side elevational view, respectively, of the cylindrical mount assembly which abut against the upper, semi-spherical surface of the endoskeletal connector member illustrated in FIG. 2a.

DETAILED DESCRIPTION OF THE DRAWINGS

The prosthetic foot illustrated as 20 in FIGS. 1, 2 and 2a includes a cantilever spring type keel, 22, (FIG. 5) over which is laid and cured a variable-thickness layer of skin-like material, 24, the latter being e.g. a soft elastomeric material or a relatively rigid polymeric material. The keel 22 is preferably made from and is generally constructed in accordance with the teachings of the the prosthetic keel as disclosed in U.S. Pat. No. 5,116,385. The resulting artificial foot member is sized to conform to the shape and size of a life-like foot. Most of keel 22 is embedded deep into—and concealed by—the flesh-like coloured elastomer 24, except at the "ankle" portion thereof where keel 22 opens freely to the outside, about a mouth 24a. An artificial limb 26 is anchored to the keel through an ankle connector member, be it of the exoskeletal type, 28 (FIG. 2), or of the endoskeletal type, 30 (FIG. 2a).

As illustrated in FIG. 5, keel 22 includes several elements from applicant's U.S. Pat. No. 5,116,385, which is to be hereby incorporated by way of reference to the present patent application. The elongated curved band keel 22 consists again of three parts, namely, an upper ankle portion 32, a forefoot end portion 36, and an intermediate heel portion 34 (the two integral portions thereof being illustrated respectively in FIGS. 5 and 6) merging the ankle portion to the forefoot end portion. The keel ankle portion 32 engages leg limb 26 via connector member 28 (FIG. 2) or 30 (FIG. 2a). The keel forefoot end portion 36 will preferably further include short transverse fore portion 38, and the coextensive intermediate arch 40, as generally disclosed in said U.S. Pat. No. 5,116,385. Similarly, intermediate heel portion 34 also preferably includes the antero-posterior medio-lateral notch or concavity 42 of said U.S. Pat. No. 5,116,385.

Now, according to the specific teachings of the present invention, the upper ankle portion 32 defines a large cavity 44 opening upwardly through its top surface 32a. Cavity 44 is preferably quadrangular so as to define a flooring 46 and four side walls 48. A large bore 50 and two similar small bores 52, 52 (one of them not being illustrated) extend through flooring 46, whereby cavity 44 opens into the volume circumscribed by the medio-lateral concavity 42 (located between the keel ankle portion 32 and the lower leg of the keel heel portion 34). A fourth small bore 56 extends through one side wall 48, preferably the side wall 48a extending directly above heel concavity 42 and generally parallel to the keel forefoot portion 36. The purpose of bore 50, and of the pair of bores 52, 52, will be later set forth.

A second specific feature of the present invention (relative to U.S. Pat. No. 5,116,385) is an additional concavity 58 made at the aft end of the intermediate section of heel portion 34. Heel part concavity 58, which is clearly apparent in FIGS. 2 and 2a and which is at least suggested in FIGS. 5 and 6, is therefore made within the sagittal plane of the prosthetic foot. Sagittal concavity 58 of heel part 34 is of a magnitude commensurate with that of medio-lateral concavity 42 thereof, i.e. extends deep (i.e. almost half of its sagittal thickness) into the intermediate arched section of heel part 34. It is understood that concavities 42 and 58 extend about planes orthogonal to one another. Aft heel concavity 58 provides temporary deformation capability along the main selected plane of the cantilever spring type keel 22. Keel 22 will yieldingly deform about both concavities 42 and 58 in a cyclical fashion during gait, i.e. ankle part 32 will tilt or "sink" downwardly and laterally outwardly at its rear part, responsively to the weight load of the user-wearer (the gap between ankle part aft end and the heel part lower end will narrow—but should not close, i.e. they should not come in contact with one another.

Clearly, as the keel ankle part 32 tiltingly sinks at the keel aft end, the centre of gravity of the user-wearer amputee will shift slightly to the rear, thus loading the keel i.e. enabling the cantilever keel to store this loading as stored deformation energy. This stored deformation energy acts as a spring and provides a mechanical feedback to the amputee enabling a better weight transfer from his sound limb to the prosthetic side.

Hence, this aft concavity 58 of cantilever keel 22 should also provide a more dampened or cushioned gait, which would be desirable as a comfort-enhancing feature when the user-wearer walks over a very hard ground surface, as well as over irregular surfaces.

FIGS. 2, 3 and 4 illustrate a first ankle connector member 28, of the exoskeletal type, for fixedly securing a prosthetic foot 20 to an artificial leg limb 26. Ankle connector member 28 includes a casing 59 sized to snugly fit inside the cavity 44 in the upper keel part 32. Casing 59 includes four bores 60, 62, 62 and 66, which, upon casing 59 being engaged into cavity 44, come in axial register with and are sized correspondingly to bores 50, the pair of bores 52, 52, and bore 56, respectively. Large coaxial bores 50 and 60 are unthreaded and freely receive the stem 70a of a known elongated bolt 70 (see especially FIG. 3).

[Conventionally, the head part of existing bolt 70 is fixedly anchored to the lower end of limb 26, while its threaded stem 70a projects therebeyond—which is to say, the bolt threaded stem 70a is not rotatable relative to limb 26]

Bore 50 includes an intermediate annular enlargement or cavity 50a, for freely receiving an annular gear wheel 72. Access to chamber 50a is enabled by a diametrally smaller countersunk bore 60a, which itself comes in register with the diametrally smallest bore 50. A cross-sectionally T-shape hollow plug 61 fits correspondingly shaped bore 60a, to freely support and retain an integral flange gear 72 in position inside casing chamber 50a. Gear wheel 72 includes gear teeth both at its inner periphery 72a and at its outer periphery 72b, as well as an axial flange 72c extending partially through the axial hollow of plug 61 and short of bore 50. Inner gear teeth 72a mesh with the threads of bolt stem 70a, while outer gear teeth 72b extend freely within annular cavity 50a of the casing through-bore 50. Thus, rotation of gear 72 induces axial displacement of casing 59 along bolt stem 70a. Casing 59 is fixedly anchored into cavity 44 by a pair of bolts 74, 74, extending through bores 52 and 62, whereby the bottom flat face of casing 59 lies flatly against the cavity flooring 46 while the top flat face of casing 59 lies flush and coplanar to the top face 32a of the keel upper ankle part 32. Hence, the bottom flat end face of leg limb 26 lies flatly against the keel top face 32a. Accordingly, the top heads of bolts 74 do not project beyond the plane of the casing top face, but rather, are embeddedly sunk into the casing 59. However, the screw nut 74a of each bolt projects slightly beneath the keel ankle part 32, but well short of the lower leg of the keel heel part 34.

Elongated bore 66 forms a channel including an intermediate portion 66a, which, as illustrated in FIG. 4, open into annular cavity 66. An elongated endless screw 76 is fitted inside channel 66 and meshes tangentially with gear 72 about intermediate channel portion 66a. Axial rotation of endless screw 76 is enabled by the provision of an Allen-key compatible head, 78, integrally projecting axially from the end of screw 76, through channel 56 and 66. The free end head 78 of screw 76 must project short of the mouth 66c of channel 66, so as not to hamper insertion of the casing 59 inside cavity 44—see FIG. 4. The endless screw 76 is retained in position within channel 66 by a cross-sectionally T-shape, hollow plug 80, located adjacent casing wall 48a about a countersunk bore section 66b of channel 66 (and preferably flush with mouth 66c).

In operation, the loose prosthetic foot 20—free from limb 26—is manually screwed to limb leg 26 by bringing the limb bolt 70 to register with and engage the main upper bore 60 of casing 59. Upon manually rotating the whole foot 20 relative to limb leg 26, the bolt stem 70a progressively engages screwingly through gear 72, and downwardly through the casing lower bore 50. Eventually, after a number of complete turns of foot 20 about the longitudinal axis of leg 26 are completed, the flat underface of the leg limb bottom end comes to flatly frictionally abut against the top faces 24a and 32a of the keel 22. When this occurs, the orientation of foot 20 may be offset relative to the sagittal plane of the leg 26. The foot 20 is then manually unscrewed and counterrotated for a fraction of a turn, up to the desired foot orientation, for example at an orientation where foot 20 becomes coplanar to the sagittal plane selected for the leg 26. At that point, the foot 20 is loose, i.e. not anchored to the leg 26 since it has been slightly unscrewed and therefore is slightly spaced from the bottom end of the leg.

This is when screw 76 intervenes. With an Allen key, the orthopedic technician engages head 78 (which is freely accessible through the enlarged bore 56 of the keel) to rotate screw 76. As screw 76 rotates, gear 72 is correspondingly entrained, driving herewith bolt 70. Since bolt 70 is integrally anchored to leg 26, gear 72 will rotate axially along bolt stem 70a without rotational motion of foot 20 relative to leg 26, thus in effect producing a tightening of the foot to the leg—i.e., the foot will again move toward and eventually come to abut against the leg 26, but now without rotation of the foot relative to the bottom flat end of the artificial leg.

The pitch of the endless screw 76 is preferably very small, to substantially prevent any time- and or wear-induced loosening of the gear 72 at the selected orientation thereof (such loosening could undesirably enable some measure of foot offsetting relative to the alignment plane of the leg).

It is understood that, with the present exoskeletal ankle connector member, the bottom leg of the keel heel part 34 does not need to be bored, as was required with prior art keels, for enabling through passage of the adjusting tool to reach the ankle connector member. This boring in prior art keels made the keels more fragile, more easily breakable transversely of the boring axis adjacent thereto. Therefore, the integrity of the keel, particularly at the heel part—which sustains the greatest cyclical loads—is not compromised, whereby the keel longevity is substantially increased.

The second embodiment of ankle connector is illustrated as 30 in FIGS. 2a and 7–10. Elements in this second embodiment which correspond to but have been modified relative to elements from the first embodiment, will be hereinafter primed ('). The keel 22 and the elastomeric covering 24 of the foot remains substantially the same as in the first embodiment. Ankle connector 30 includes a generally semi-spherical Stub part, 82, and an integral box-like casing 72' depending from the flat face 82a of stub 82. The casing part 72' of ankle connector 30 is engaged into the keel heel part cavity 44, and anchored thereto by bolts 74'.

Stub 82 includes the conventional endoskeletal apex projection 84, extending on the side opposite keel 22, into artificial leg 26'. The orientation of the leg 26' relative to foot 22 is adjusted by means of a few (e.g. four as illustrated) set screws 86, which endwisely engage projection 84 transversely thereof. Screws 86 threadingly engage a corresponding number of threaded bores 88 made across a cylindrical tube 90 (FIGS. 11–12), this tube 90 being in turn anchored to the tubular core 96 of leg 26' via bolts 92 engaging tube ears 94. More particularly, the lower portion of tube 96 engages into the hollow of diametrally larger tube 90, and ears 94 form a tightening collar that frictionally interlock tubes 90 and 96 when screws 92 are tightened. Set screws 86 are readily accessible for adjustment, without the need of boring transversely through the skin-like hull of leg 26', since the hull cover is installed around axial tube 96 only after final anchoring adjustment of the respective ankle connector 28 or 30 between the foot and the limb.

Hence, the joint of the endoskeletal ankle connector is located inside the hollow of artificial leg 26', at the interplay of the stub shaft 90 with the set screws 86.

Again, with this endoskeletal ankle connector 30, there is no need for piercing a hole in the lower part of the keel heel part, in order to reach the overlying keel cavity 44, since the casing part 72' of the ankle connector 30 is simply anchored in position by bolts 74', with each bolt head being located on the top side of the foot 20.

It is understood that either the exoskeletal or the endoskeletal ankle connectors includes a casing member, 72 or 72', destined to engage into and be anchored within a single same cavity 44 in the ankle part of a cantilever spring type prosthetic keel. Hence, in each case, the structural integrity of the keel is not compromised, since such keel and ankle connector construction alleviates the requirement of boring the lower leg of the keel heel part for enabling access by the ankle connector tightening tool, as was required with prior art ankle connectors.

It is also understood that, although only a right-hand side prosthetic foot has been illustrated in the present drawings, it is considered to be well within the scope of the present invention to install either endo- or exo-skeletal ankle connector members 30, 28, respectively to a left-hand side prosthetic foot, which is simply a mirror image of the right-hand side foot.

We claim:

1. An exoskeletal ankle connector for use in fixedly securing a prosthetic foot to a prosthetic leg, said foot of the type having an elongated cantilever spring type keel, said keel to be of the type defining an elongated forefoot part, an ankle part and a heel part merging said ankle part with said forefoot part, said keel ankle part to be provided with a cavity, said leg to be of the type having a bottom end with an integral bolt with said bolt having a free projecting threaded stem;

said ankle connector consisting of:
(a) a casing member, sized to conformingly engage into and snugly fit within said keel cavity;
(b) anchoring means, for releasably anchoring said casing member to said keel inside said keel cavity;
(c) screw means, to progressively draw toward one another said casing member and said leg bottom end along said bolt stem upon inducing rotation of said foot relative to said leg; and
(d) tightening means, cooperating with said screw means to anchor said foot at a selected angular orientation relative to said leg upon said foot remaining rotationless relative to said leg;

wherein there is free operative access to said tightening means;

wherein said casing member further includes a first unthreaded channel with an enlarged intermediate annular chamber, said first channel for free through engagement by said leg bolt stem; said screw means defining an annlar gear freely mounted within and retained by said annular chamber and defining radially inward teeth, said gear inward teeth for threadingly engaging said leg bolt threaded stem.

2. An exoskeletal ankle connector as defined in claim 1, wherein said selected angular orientation of the prosthetic foot is within the sagittal plane of the leg.

3. An ankle connector as defined in claim 1, wherein said casing member further includes a second channel extending orthogonally of said first channel, said second channel opening into said annular chamber about an intermediate section of said second channel; said keel to include a boring in coaxial register with said second channel for enabling external access thereto, said keel boring to extend transversely of the plane of said selected angular orientation; said annular gear further defining a radially outward concave surface provided with teeth; said tightening means defining an endless screw, extending inside said second channel for frictional rotational engagement within the casing member, said endless screw defining teeth threadingly engaging with said gear radially outward teeth tangentially of said annular gear;

wherein cooperation of said endless screw with said annular gear provides tightening of said foot to said leg without any rotation of said foot relative to said leg for achieving a fine degree of adjustment in the orientation of said foot within said selected angular orientation thereof.

4. An ankle connector as defined in claim 3, wherein said endless screw teeth define a very short pitch, to substantially prevent any by timeborne wear induced loosening of said annular gear about said leg bolt stem.

* * * * *